United States Patent [19]

Shaw et al.

[11] 4,091,813

[45] May 30, 1978

[54] SURGICAL INSTRUMENT HAVING SELF-REGULATED ELECTRICAL PROXIMITY HEATING OF ITS CUTTING EDGE AND METHOD OF USING THE SAME

[75] Inventors: Robert F. Shaw, San Francisco, Calif.; David E. Stutz, Columbus, Ohio

[73] Assignee: Robert F. Shaw, Portola Valley, Calif.

[21] Appl. No.: 558,334

[22] Filed: Mar. 14, 1975

[51] Int. Cl.² ............................................. A61B 17/38
[52] U.S. Cl. ................................. 128/303.14; 30/140; 219/233
[58] Field of Search .......... 30/140; 128/303.1, 303.13, 128/303.14; 219/10.49, 10.57, 221, 223, 227, 228, 229, 230, 231, 233, 241

[56] References Cited

U.S. PATENT DOCUMENTS

| 1,805,904 | 5/1931 | Carpenter | 128/303.14 |
|---|---|---|---|
| 1,975,437 | 10/1934 | Sorrel | 219/10.49 |
| 2,863,036 | 12/1958 | Mitchell et al. | 30/140 |
| 3,024,342 | 3/1962 | Birnbach et al. | 30/140 |
| 3,489,884 | 1/1970 | Waselewski, Jr. | 219/241 UX |
| 3,515,837 | 6/1970 | Ando | 219/10.49 |
| 3,524,966 | 8/1970 | Ando | 219/10.49 X |
| 3,768,482 | 10/1973 | Shaw | 128/303.1 |

FOREIGN PATENT DOCUMENTS 1,157,711  7/1969  United Kingdom ............. 219/10.49

OTHER PUBLICATIONS

Murakami, K., "The Characteristics of Ferrite Cores With Low Curie Temperature," in IEEE Trans. on Magnetics, June 1965, pp. 96–100.
Bennett; Edward, "The Proximity Effect: Its Application, etc.," in Trans. AIEE, 51:621 – 627, 1932.
Bennett; Edward, "Concentration of Heating Currents," in Electrical Engineering, Aug. 1932, pp. 559 – 562.

*Primary Examiner*—Robert W. Michell
*Assistant Examiner*—Michael H. Thaler
*Attorney, Agent, or Firm*—Lyon & Lyon

[57] ABSTRACT

The cutting edge of a scalpel blade is heated to a preselected constant temperature range by conduction of high frequency current through the blade of ferromagnetic material in a region thereof which is in close proximity to a conductor positioned along the cutting edge. Selective heating of regions of the cutting edge that are locally cooled by the tissue contact during surgical cutting is provided by constructing the blade of ferromagnetic materials that have a Curie point in the operating temperature range and that provide large increases in magnetic permeability for temperature decrements below the Curie point.

65 Claims, 2 Drawing Figures

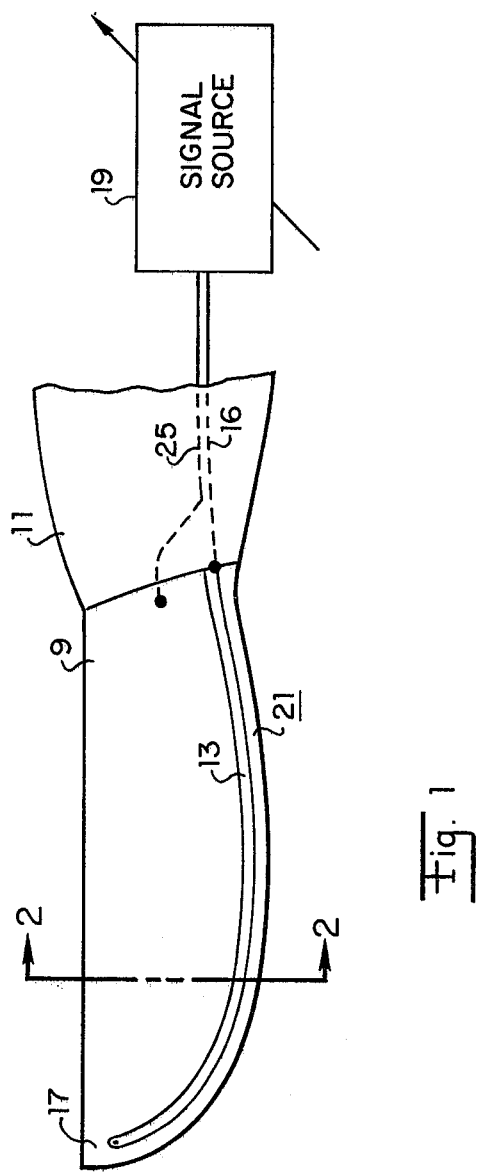
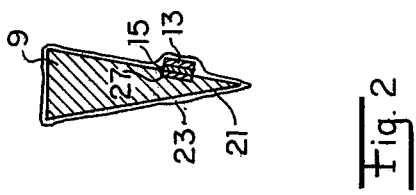

SURGICAL INSTRUMENT HAVING SELF-REGULATED ELECTRICAL PROXIMITY HEATING OF ITS CUTTING EDGE AND METHOD OF USING THE SAME

BACKGROUND OF THE INVENTION

The control of bleeding during surgery accounts for a major portion of the total time involved in an operation. The bleeding that occurs from the plethora of small blood vessels that pervade all tissues whenever tissues are incised obscures the surgeon's vision, reduces his precision, and often dictates slow and elaborate procedures in surgical operations. It is well known to heat the tissues to minimize bleeding from incisions, and surgical scalpels which are designed to elevate tissue temperatures and minimize bleeding are also well known. One such scalpel transmits high frequency, high energy sparks from a small electrode held in the surgeon's hand to the tissues, where they are converted to heat. Typically, substantial electrical currents pass through the patient's body to a large electrode beneath the patient, which completes the electrical circuit. Discharge of sparks and temperature conversion in the tissue are poorly controlled in distribution and intensity, and erratic muscular contractions in the patient are produced so that this apparatus cannot be used to perform precise surgery. Further, apparatus of this type frequently produce severe tissue damage and debris in the form of charred and dead tissue, which materially interfere with wound healing.

Another well-known surgical scalpel employs a blade with a resistive heating element which cuts the tissue and provides simultaneous hemostasis. Although these resistive elements can be readily brought to a suitably high and constant temperature in air prior to contacting tissues, as soon as portions of the blade come in contact with tissues, they are rapidly cooled. During surgery, non-predictable and continuously varying portions of the blade contact the tissues as they are being cut. As the blade cools, the tissue cutting and hemostasis become markedly less effective and tissue tends to adhere to the blade. If additional power is applied by conventional means to counteract this cooling, this additional power is selectively delivered to the uncooled portions of the blade, frequently resulting in excessive temperatures which may result in tissue damage and blade descruction. This results from the fact that in certain known resistively heated scalpels, the heating is a function of the current squared times the resistance ($I^2R$). In conventional metallic blades of this type, the higher the temperature of any blade portion, the greater its electrical resistance, and consequently the greater the incremental heating resulting from incremental power input.

It is generally recognized that to seal tissues and effect hemostasis it is desirable to operate at a temperature between 300° C. and 1000° C. And for reasons noted above, it is desirable that electrothermal hemostatic surgical cutting instruments include a mechanism by which power is selectively delivered to those portions of the blade that are cooled by tissue contact so that the cutting edge may be maintained at a substantially uniform operating temperature within the desired optimal range. Recently, hemostatic scalpels have been described (see, for example, U.S. Pat. Nos. 3,768,482 and 3,826,263) in which the temperature-controlling mechanisms include resistive heating elements disposed on the surface of the scalpel blade. However, such instruments require precision in fabricating the dimensions of the heating elements to obtain the desired resistances. And such resistive heating elements may be subjected to variations in resistance during use, as tissue juices and proteins become deposited upon the surface of the blade.

SUMMARY OF THE INVENTION

The present invention provides a surgical cutting instrument in which the cutting portion of the blade is brought to and maintained within an elevated preselected temperature range by heating of the internal structure of the blade.

When closely-coupled conductors are energized by alternating currents of radio frequencies, the return current in one conductor has a tendency to flow in close proximity to the forward current in the other conductor, a characteristic which is known as the "proximity" effect.

According to the present invention, a scalpel blade is fabricated of an electrically conductive material, and an alternating current-carrying conductor is disposed on the surface of the blade and insulated from it except at its distal end. An applied radio frequency (RF) signal causes the return current to flow only through that portion of the blade material contiguous to and essentially only within the width of the forward current-carrying conductor. This return current will tend to be concentrated near the surface of the blade material with current density that decreases exponentially with distance from the overlying surface. The skin depth is defined as the depth at which current density is 37% of its surface value, and it is determined by the electrical resistivity and the magnetic permeability of the material and by the frequency of the alternating current. Thus, the $I^2R$ Joule heating of the blade is independent of thickness variations of the forward current-carrying surface conductor, and the average temperature of the cutting edge is adjustable by adjustments to the amplitude and/or frequency of the applied RF signal.

Further, selective heating of those portions of the cutting edge that are cooled by tissue contact in order to maintain cutting edge temperatures sufficiently constant (i.e. temperature self-regulation) may be accomplished by fabricating the blade of a material which exhibits substantial changes in electrical parameters such as permeability or electrical resistivity as a function of temperature. Since the skin depth is inversely related to the square root of the magnetic permeability, an increase in magnetic permeability in the portions of the blade edge that are cooled upon contact with tissue will decrease the skin depth, thus decreasing the cross-sectional area (path width times skin depth) and causing an increase in the resistance (or current flux) of the cooled portions and an increase in the Joule heating thereof.

By way of example, ferromagnetic materials composed of iron, nickel, and cobalt and their alloys exhibit large changes in relative permeability as their temperature goes through a transition point called the "Curie" point. In many iron-nickel alloys this Curie point occurs in the temperature range of interest. Above the Curie point, the relative permeability may be near unity and at temperatures below the Curie point the permeability may rapidly increase by factors of 100 to 1000 for magnetic field strengths of the dimension that would be utilized in this application. Thus, if the scalpel is operated at a temperature somewhat above the Curie point, as various portions of the blade are cooled by contact with the tissues, the temperature of those and only those portions of the blade will tend to drop below the Curie point, at which time the permeability of the material in that region will increase by 100 to 1000 with resultant increases in the heating of the cooled portions by factors of 10 to 30.

Similarly, if the blade material has a negative temperature coefficient of resistance, the region of the blade edge cooled by tissue contact will undergo an increase in resistance and a resultant increase in the Joule heating thereof. By way of example, various semiconductors, such as silicon and germanium, and compounds thereof, and various electrolytic ceramics such as β alumina zirconia, exhibit such negative temperature coefficients of resistance.

DESCRIPTION OF THE DRAWINGS

FIG. 1 is a side view of the electrically heated surgical scalpel; and

FIG. 2 is an end sectional view of the scalpel blade of the apparatus of FIG. 1.

DESCRIPTION OF THE PREFERRED EMBODIMENT

Referring now to FIGS. 1 and 2 there is illustrated one embodiment of the invention in which a blade portion 9 made of an electrically conductive material is attached to a handle portion 11 to form the surgical instrument. A current-carrying conductor 13 is disposed on the blade 9 adjacent the cutting edge 21 and is insulated therefrom by a layer of insulation 15 substantially along the length of the conductor 13, except at the remote end 17 where the conductor 13 is connected to the blade 9. When power is applied from the radio frequency signal source 19 through connections 25 and 16 to the circuit consisting of the conductor 13 and blade 9, the return current path 27 through blade 9 will flow substantially within the skin depth along a path that will be about the same width as the high frequency current-carrying conductor 13 and that will be proximate thereto along its length. The high frequency return current in blade 9 will heat current path 27 adjacent the cutting edge 21 to a temperature which can be controlled by the power input from the high frequency signal source 19.

Self-regulation of the operating temperature is achieved by making the blade 9 of a ferromagnetic material which has a Curie point that is below the desired temperature of the cutting edge prior to cutting but that is well within the acceptable operating temperature range. As tissue cutting is initiated, the regions of the cutting edge which contact the tissue may be cooled to the Curie point temperature or below, thus producing in the cooled regions an increase in magnetic permeability which will decrease skin depth and decrease the cross-sectional area of the current path 27 within the blade 9. This will increase the resistance and increase power dissipation and heating of the regions of the blade that are cooled by contact with tissue.

The following table indicates some values of power dissipation in a scalpel blade 3 cm. long and 10 mils thick made from a 50-50 iron-nickel alloy in which the surface conductor 13 is 40 mils wide and the scalpel is energized with a current of about 7 amperes at 6 megahertz. This RF signal current may be maintained constant where desired using conventional circuitry of well-known design.

| Material | Resistivity, ohm-cm($10^{-6}$) | | Skin Depth in ($10^{-3}$) | | Relative Permeability | | Power, Watts/cm of Blade Length | |
|---|---|---|---|---|---|---|---|---|
| | 500° C. | 400° C. | 500° C. | 400° C. | 500° C. | 400° C. | 500° C. | 400° C. |
| 50-50 Fe-Ni | 105 | 100 | 8.3 | 0.81 | 1 | 100 | 2.41 | 23.5 |

It is evident that there is nearly a tenfold increase in power dissipation when and where the temperature decreases below the Curie point. The Curie point temperatures, resistivities, relative permeabilities and changes in permeability as a function of temperature may be varied by altering the composition of the material used in the blade 9 or by altering the percentages of elements that form the alloy material of blade 9.

The high frequency signal source 19 may be adjustable in signal amplitude or in frequency, or both, to establish the operating temperature of the cutting edge in air.

In FIG. 2, there is shown a sectional view of the blade 9 including the conductor 13 disposed on one surface of blade 9 near the cutting edge thereof. A layer of insulating material 23 is shown disposed over the conductor 13 and blade 9 to insulate them from the tissue being cut. For optimal temperature self-regulation, the blade thickness in the region of the return current path 27 should be somewhat in excess of the maximum skin depth of current path 27 in the operative temperature range.

In another embodiment of the present invention, the conductive material of blade 9 exhibits a negative temperature coefficient of resistance to provide increased power dissipation from the return current 27 in those regions of the cutting edge that are cooled upon contact with tissue being cut.

Thus, the proximity-heated, electrothermal scalpel is especially advantageous where a very thin self-regulating blade is desired for cutting tissue with simultaneous hemostasis.

We claim:

1. A blade comprising:
   a cutting means including a cutting edge having an electrically conductive material disposed in the region of said cutting edge; and
   an electrical conductor means disposed adjacent the cutting edge and between distal and proximal ends of said cutting means, said electrical conductor means being disposed in electromagnetically coupled and electrically insulated relationship to said electrically conductive material and being conductively connected to the material only near the distal end of the cutting means (edge) for providing a conductive path through the material along said cutting means (edge) between the conductive connection to said electrical conductor means and the proximal end of said cutting means (edge).

2. A hemostatic cutting device as in claim 1 wherein said material has an electrical parameter that varies as a function of temperature to increase power dissipation on applied electrical signal in the regions of the cutting edge which are selectively cooled.

3. A blade as in claim 2 wherein the material has a thermal coefficient of resistance which varies inversely with temperature.

4. A blade as in claim 1 wherein said material has a permeability which varies inversely with temperature.

5. A blade as in claim 1 wherein said material exhibits a Curie point about which a transition in permeability with temperature occurs.

6. A blade as in claim 4 wherein said material exhibits a Curie point about a temperature within the range of 300° C. to 1000° C.

7. A blade as in claim 1 wherein said material includes ferromagnetic material.

8. A blade as in claim 1 wherein said material includes an element selected from the group consisting of iron, nickel and cobalt.

9. A blade as in claim 1 comprising a layer of insulation disposed over said blade and over said electrical conductor means.

10. The hemostatic cutting device claimed in claim 1 wherein the thickness of said blade in the region of said conductive current path is greater than the maximum skin depth of said conductive current path.

11. A blade as in claim 1 wherein the material of said cutting means is capable of varying the skin depth of the conducting path for alternating electrical current therethrough.

12. A blade as in claim 1 comprising circuit means coupled to the proximal end of said electrical conductor means and to the proximal end of said cutting means for applying alternating signal thereto.

13. A blade as in claim 1 comprising:
sensor means responsive to the temperature of a region along the cutting edge for producing a representative control signal; and
means responsive to the control signal for altering a selected parameter of an alternating signal applied to the electrical conductor means from the circuit means.

14. A blade as in claim 13 wherein the means responsive to the control signal alters one of the amplitude and frequency of the alternating signal from the circuit means.

15. A blade as in claim 1 wherein the thickness of the cutting means in the region of said conductive current path is greater than the maximum skin depth of the conductive current path.

16. A blade as in claim 1 wherein the material of the cutting means includes a semiconductor material.

17. A blade as in claim 1 wherien the material of the cutting means includes one of the elements of the group consisting of silicon and germanium and compounds thereof.

18. A blade as in claim 1 wherein the material of the cutting means includes electrolytic ceramic.

19. A blade as in claim 1 wherein the material of the cutting means includes beta alumina zirconia.

20. A blade as in claim 1 wherein said conductive path is utilized to elevate the temperature in the region of the cutting edge.

21. A surgical blade (instrument) for cutting tissue with simultaneous hemostasis, (the instrument) comprising:
a cutting (element) means of electrically conductive material having a tissue-cutting edge, said material containing a metal being selected from a group consisting of iron, nickel, and cobalt and exhibiting a Curie point about a temperature within the range of 300° C to 1,000° C; and
an electrical conductor means disposed near said tissue cutting edge between distal and proximal ends of said cutting means (thereof), said electrical conductor means being disposed in electromagnetically coupled and electrically insulated relationship to said material of said cutting (element) means and being conductively connected to said cutting (element) means only near the distal end of said (tissue) cutting means for providing a conductive current path through the material of said cutting means between the conductive connection to said electrical conductor and the proximal end of said cutting means;

22. The surgical blade claimed in claim 21 further comprising a layer of insulation disposed over said cutting and over said electrical conductor means for insulating tissue being cut from said surgical instrument.

23. A hemostatic scalpel blade comprising:
a cutting means including a tissue-cutting edge of electrically conductive material; and
an electrical conductor means disposed near said tissue-cutting edge between distal and proximal ends of said cutting means, said electrical conductor means being disposed in electromagnetically coupled and electrically insulated relationship to the material of said cutting means and being conductively connected to said cutting means only near the distal end of said cutting means for providing a conductive current path through the material of said cutting means between the conductive connection to said electrical conductor means and the proximal end of said cutting means.

24. The hemostatic scalpel blade claimed in claim 23 wherein said material of said cutting means has an electrical parameter that varies as a function of temperature to increase power dissipation in the regions of said tissue-cutting edge which are selectively cooled upon contact with tissue being cut.

25. The hemostatic scalpel blade claimed in claim 23 wherein the material of said cutting means has a permeability which varies inversely with temperature.

26. The hemostatic scaplel blade claimed in claim 25 wherein the material of said cutting means exhibits a Curie point about which a transition in permeability with temperature occurs.

27. The hemostatic scalpel blade claimed in claim 26 wherein the material of said cutting means exhibits a Curie point about a temperature within the range of 300° C. to 1,000° C.

28. The hemostatic scalpel blade claimed in claim 23 wherein said cutting means includes ferromagnetic material.

29. The hemostatic scalpel blade claimed in claim 23 wherein said material of said cutting means includes an element selected from the group consisting of iron, nickel and cobalt.

30. The hemostatic scalpel blade claimed in claim 23 further comprising a layer of insulation disposed over said cutting means and over said electrical conductor means for insulating tissue being cut from said hemostatic scalpel blade.

31. The hemostatic scalpel blade claimed in claim 23 wherein the material of said cutting means has a thermal coefficient of resistance which varies inversely with temperature.

32. The hemostatic scalpel blade claimed in claim 23 wherein the thickness of said cutting means in the region of said conductive current path is greater than the maximum skin depth of said conductive current path when said cutting blade is operated between about 300° C. and about 1,000° C.

33. A hemostatic surgical cutting blade as in claim 23 wherein said material has a coefficient of resistance which varies inversely with temperature.

34. A hemostatic scalpel blade comprising:
a cutting means including a tissue-cutting edge of electrically conductive material and being further described as including a metal selected from the group consisting of iron, nickel and cobalt and having an electrical parameter that varies as a function of temperature to increase power dissipation in the regions of said tissue-cutting edge which are selectively cooled upon contact with tissue being cut; and
an electrical conductor means disposed near said tissue-cutting edge between distal and proximal ends of said cutting edge, said electrical conductor means being disposed in electromagnetically coupled and electrically insulated relationship to the material of said cutting blade and being conductively connected to said cutting (blade) means only near the distal end of said (tissue-) cutting means (edge) for providing a conductive current path through the material of said cutting (blade) means between the conductive connection to said electrical conductor means and the proximal end of said (tissue-) cutting means (edge).

35. The hemostatic scalpel blade claimed in claim 34 wherein the material of said cutting means has a permeability which varies inversely with temperature.

36. The hemostatic scalpel blade claimed in claim 34 wherein the material of said cutting means exhibits a Curie point about which a transition in permeability with temperature occurs.

37. The hemostatic scalpel blade claimed in claim 34 further comprising a layer of insulation disposed over said cutting means and over said electrical conductor means for insulating tissue being cut from said hemostatic scalpel blade.

38. A method of utilization of a hemostatic scalpel blade having a cutting blade of electrically conductive material and an electrical conductor means disposed between the distal and proximal ends of said blade comprising:
insulating said electrical conductor from said cutting blade except at said distal blade end;
passing electrical current through said electrical conductor thereby heating said cutting blade;
contacting tissue with said cutting blade; and
thereby cauterizing said tissue contacted by said cutting blade.

39. The method of utilization of a hemostatic scalpel blade claimed in claim 38 further comprising:
increasing power dissipation in the regions of said cutting blade which are selectively cooled upon contact with the tissue being cut responsive to the permeability of said electrically conductive material which varies inversely with temperature between about 300° C. and about 1,000° C.

40. The method of cutting using a blade having a cutting means with a cutting edge operating at an elevated temperature, the method including the steps of:
conducting an alternating current through an electrical conductor which is disposed along the cutting edge; and
conducting current in a return path through the blade substantially only in close proximity to the cutting edge of the cutting means which is disposed in electromagnetically coupled and electrically insulated relationship to the electrical conductor.

41. The method of cutting as in claim 40 wherein said cutting means includes means for increasing the power dissipation on applied electrical signal in the regions of the cutting edge when said regions of said cutting edge are selectively cooled.

42. The method of cutting as in claim 40 wherein in the step of conducting current, the skin depth of the alternating current conductor path through the cutting means is varied as a function of the temperature of the return path in close proximity to the electrical conductor.

43. The method of cutting as in claim 42 wherein in the step of conducting current, the skin depth varies inversely with temperature.

44. The method of cutting as in claim 40 wherein in the step of conducting current, the thermal coefficient of resistance of the material of the cutting means varies inversely with temperature.

45. The method of cutting as in claim 40 wherein in the step of conducting current, one of the frequency and amplitude of an alternating electrical signal is altered in response to changes in temperature along the cutting edge.

46. The method of cutting as in claim 40 wherein in the step of conducting current, the permeability of the material of the cutting means varies inversely with temperature.

47. The method of cutting as in claim 40 wherein the step of conducting current, the material of the cutting means exhibits a Curie about which a transition in permeability with temperature occurs.

48. A hemostatic surgical blade comprising:
a cutting means including a tissue-cutting edge having an electrically conductive material disposed in the region of said cutting edge; and
an electrical conductor means disposed adjacent the cutting edge and between distal and proximal ends of said cutting means, said electrical conductor means being disposed in electromagnetically coupled and electrically insulated relationship to said electrically conductive material and being conductively connected to the material only near the distal end of the cutting means for providing a conductive path through the material along said cutting means between the conductive connection to said electrical conductor means and the proximal end of said cutting means.

49. A surgical blade as in claim 48 wherein the material of the cutting means is capable of varying the skin depth of the conducting path for alternating electrical current therethrough.

50. A surgical blade as in claim 48 comprising circuit means coupled to the proximal end of said electrical conductor means and to the proximal end of cutting means for applying alternating signal thereto.

51. A surgical blade as in claim 48 comprising:
sensor means responsive to the temperature of a region along the cutting edg for producing a representative control signal; and means resonsive to the control signal and altering a selected parameter of an alternating signal applied to the electrical conductor means from the circuit means.

52. A surgical blade as in claim 48 wherein the means resonsive to the control signal alters one of the amplitude and frequency of the alternating signal from the circuit means.

53. A surgical blade as in claim 48 wherein the thickness of the cutting means in the region of said conductive current path is greater than the maximum skin depth of the conductive current path when the cutting means is operated in a selected temperature range between about 300° C and about 1000° C.

54. A surgical blade as in claim 48 wherein the material of the cutting means includes a semiconductor material.

55. A surgical blade as in claim 48 wherein the material of the cutting means includes one of the elements of the group consisting of silicon and germanium and compounds thereof.

56. A surgical blade as in claim 48 wherein the material of the cutting means includes electrolytic ceramic.

57. A surgical blade as in claim 48 wherein the material of the cutting means includes beta alumina zirconia.

58. The method of homostatic cutting using a cutting means having a cutting edge operating at an elevated temperature, the method including the steps of:
   conducting an alternating current through an electrical conductor which is disposed along the cutting edge; and
   conducting current in a return path through the blade substantially only in close proximity to the cutting edge of the blade which is dispoed in electromagnetically coupled and electrically insulated relationship to the electrical conductor.

59. A method of hemostatic cutting as in claim 56 wherein said cutting means includes means for increasing the power dissipation on applied electrical signal in the regions of the cutting edge when said regions of said cutting edge are selectively cooled.

60. The method of hemostatic cutting as in claim 59 wherein in the step of conducting current, the skin depth varies inversely with temperature.

61. The method of hemostatic cutting as in claim 58 wherein in the step of conducting current, the skin depth of the alternating current conductor path through the cutting means is varied as a function of the temperature of the return path in close proximity to the electrical conductor.

62. The method of hemostatic cutting as in claim 58, wherein in the step of conducting current, the thermal coefficient of resistance of the material of the cutting means varies inversely with temperature.

63. The method of hemostatic cutting as in claim 58 wherein in the step of conducting current, one of the frequency and amplitude of an alternating electrical signal is altered in response to changes in temperature along the cutting edge.

64. The method of hemostatic cutting as in claim 58 wherein in the step of conducting current, the permeability of the material of the cutting means varies inversely with temperature.

65. The method of hemostatic cutting as in claim 58 wherein the step of conducting current, the material of the cutting means exhibits a Curie point about which a transition in permeability with temperature occurs.

* * * * *